United States Patent [19]

Green et al.

[11] Patent Number: 5,414,092
[45] Date of Patent: May 9, 1995

[54] THIOXANTHONE DERIVATIVES

[75] Inventors: William A. Green; Allan W. Timms, both of Widnes, United Kingdom

[73] Assignee: International Bio-Synthetics Limited, United Kingdom

[21] Appl. No.: 205,727

[22] Filed: Mar. 4, 1994

Related U.S. Application Data

[63] Continuation of Ser. No. 897,666, Jun. 12, 1992, abandoned.

[30] Foreign Application Priority Data

Jun. 24, 1991 [GB] United Kingdom ............... 9113580

[51] Int. Cl.$^6$ ............................................. C07D 335/12
[52] U.S. Cl. ..................................................... 549/27
[58] Field of Search ........................................... 549/27

[56] References Cited

U.S. PATENT DOCUMENTS 4,661,595  4/1987  Ávár ................................... 546/89

FOREIGN PATENT DOCUMENTS 105678  8/1980  Japan .

*Primary Examiner*—Richard L. Raymond

[57] ABSTRACT

Thioxanthone derivatives of the general formula I

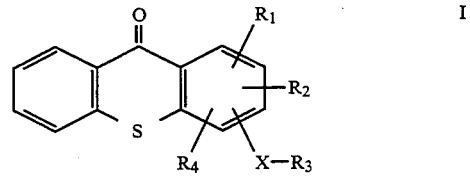

wherein $R^1$ wherein $R^1$ represents a halogen atom or a $C_{1-10}$ alkoxy group, $R^2$ and $R^4$ each represent a hydrogen atom, a halogen atom or a $C_1$–$C_6$ alkyl group, X represents oxygen or sulphur, and $R^3$ represents a $C_1$–$C_{10}$ alkyl group optionally substituted by a hydroxy group which hydroxy group may be alkylated by an optionally substituted $C_{1-6}$ alkyl, $C_{1-6}$ alkenyl or a benzyl group or acylated by a $C_{1-8}$ alkanoyl or $C_{1-8}$ alkenoyl group, a $C_{1-10}$ alkenyl group, a $C_3$–$C_6$ cycloalkyl group, a $C_1$–$C_8$ alkanoyl group, a $C_{1-8}$ alkenoyl group, an optionally substituted phenyl group, an optionally substituted benzyl group or an optionally substituted benzoyl group. Process for the preparation of the above thioxanthones, their use as photoinitiators, photopolymerisable compositions containing them, the use of such compositions for the production of photocured surface coating and products on which these photocured compositions have been applied.

25 Claims, No Drawings

THIOXANTHONE DERIVATIVES

This is a continuation of application Ser. No. 07/897,666 filed on Jun. 12, 1992, now abandoned.

The invention relates to thioxanthone derivatives, their preparation, their use as photoinitiators, photopolymerisable compositions containing them, the use of such compositions for the production of photocured surface coatings and products on which these photocured compositions have been applied.

Prior art photoinitiators include substituted thioxanthones such as 2-chlorothioxanthone and, in particular, 2-isopropyl-thioxanthone. These compounds are widely used in the field of pigmented photocurable surface coatings and inks. Two important techniques in which these photoinitiators are used are lithographic printing and screen printing.

The lithographic printing process involves the separation of a (photocurable) ink/water phase to form an image which is transferred via a system of rollers to the substrate, which is usually paper or card, followed by photocuring of the ink layer on the substrate. The process requires high line speeds to be efficient and thus a fast photocurable reaction is essential.

The screen printing process involves passing (a photocurable) ink through a screen mesh which is negatively blocked out so that a positive image appears on the substrate under the mesh, followed by photocuring of the ink layer on the substrate. This process gives rise to heavier, thicker depositions of the ink on the substrate when compared with other printing processes, the heavier, thicker depositions resulting in brighter, stronger colours. The screen process is used for posters, banners, signs etc. and the process requires good depth hardness to be developed during photocuring to give the ink layer on the substrate good stability.

There have now been discovered certain novel thioxanthone derivatives which give increased photocuring speed in the lithographic printing process and increased depth cure in the screen printing process.

According to the present invention there are provided thioxanthone derivatives of the general formula I

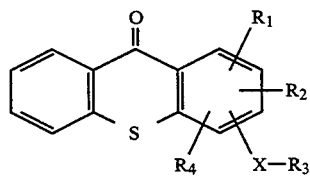

wherein $R^1$ represents a halogen atom or a $C_{1-10}$ alkoxy group, $R^2$ and $R^4$ each represent a hydrogen atom, a halogen atom or a $C_1-C_6$ alkyl group, X represents oxygen or sulphur, and $R^3$ represents a $C_1-C_{10}$ alkyl group optionally substituted by a hydroxy group which hydroxy group may be alkylated by a $C_{1-6}$ alkyl or a benzyl group or acylated by a $C_{1-8}$ alkanoyl or $C_{1-8}$ alkenoyl group, a $C_{1-10}$ alkenyl group, a $C_3-C_6$ cycloalkyl group, a $C_1-C_8$ alkanoyl group, a $C_{1-8}$ alkenoyl group an optionally substituted phenyl group, an optionally substituted benzyl group or an optionally substituted benzoyl group.

$R^1$ suitably represents a fluorine, chlorine, bromine or iodine atom or a $C_{1-4}$ alkoxy, and is preferably a chlorine or bromine atom or a methoxy group, more preferably a chlorine atom. $R^1$ is preferably attached to the 1- or 3-position of the thioxanthone molecule, more preferably the 1-position.

$R_2$ and $R_4$ each suitably represent a hydrogen, fluorine, chlorine, bromine or iodine atom or a $C_{1-4}$ alkyl group, preferably a hydrogen, chlorine or bromine atom or a methyl group, more preferably a hydrogen atom or a methyl group. $R_2$ especially represents a hydrogen atom or a methyl group at the 2-position and $R_4$ especially represents a hydrogen or chlorine atom or a methyl group at the 3-position, preferably a hydrogen atom.

X preferably represents an oxygen atom, more preferably an oxygen atom at the 4-position. $R_3$ especially represents a $C_1-C_6$ alkyl or a $C_{2-6}$ alkenoyl group, a $C_{1-5}$ alkanoyl group, a $C_{1-5}$ alkenoyl group or a phenyl, benzyl or benzoyl group, preferably a propyl group. When $R_3$ represents an alkyl group, this group may be substituted by a hydroxy group, which hydroxy group may be alkylated by a $C_{1-4}$ alkyl or a benzyl group or acylated by a $C_{1-5}$ alkanoyl or $C_{1-5}$ alkenoyl group. In case $R_3$ represents a substituted phenyl group, a substituted benzyl group or a substituted benzoyl group suitable substituents are halogen atoms, cyano group, $C_1-C_{10}$ alkyl groups, especially $C_{1-4}$ alkyl group; $C_1-C_{10}$ alkoxy groups, especially $C_{1-4}$ alkoxy groups and nitro groups.

Compounds of the general formula I may be prepared conveniently by a two step process from readily available materials. In the first step a substituted hydroxy- or thio-thioxanthone (mercaptothioxanthone) is prepared by ring closure from 2,2'-dithiobisbenzoic acid or 2-mercapto benzoic acid or a derivative thereof and a phenolic- or thio-phenolic compound. In the second step the ether or thioether is formed by reacting the hydroxy or thiohydroxy group with an alkylating or acylating agent. The invention therefore also relates to a process for the preparation of thioxanthone derivatives of the general formula I as defined herein before, which comprises reacting 2,2'-dithiobisbenzoic acid or 2-mercapto benzoic acid or a derivative thereof and a substituted phenol or thiophenol to form a substituted hydroxy or thio-thioxanthone compound, followed by reaction of the hydroxy or thio compound with an alkylating or an acylating compound. The alkylating compound is preferably an alkyl halide, more preferably an alkyl bromide or an alkyl iodide, and the acylating compound is preferably an acyl halide, more preferably an acyl chloride. The derivative of 2-mercapto benzoic acid is suitably the acid chloride.

The invention further relates to the use of a thioxanthone derivative of the general formula I as described hereinbefore as a photoinitiator in photocurable compositions.

Another aspect of the invention relates to photocurable compositions comprising a solution or dispersion of at least one polymerisable monomer or oligomer and, as photoinitiator, a thioxanthone derivative of the general formula I as described hereinbefore. The composition usually will comprise 0.5 to 10% by weight of photoinitiator. Suitable photopolymerisable prepolymers include acrylated epoxides, polyesters and polyurethanes. The prepolymers are usually combined with monomers for viscosity control. Suitable monomers are low weight acrylates, which may be mono-, di- or tri-functional.

To increase the photosensitivity still further it is preferred to add a tertiary nitrogen compound to the composition, suitably in an amount between 0.5 and 8% wt, preferably between 1 and 4% wt. Suitable compounds are triethanolamine, methyl-diethanolamine, ethyldiethanolamine and esters of dimethylamino benzoic acid. These compounds behave as co-initiators or accelerators for the primary photoinitiator and increase the efficiency and speed of the crosslinking process.

The invention also relates to the use of the above described compositions in the production of photocurable surface coatings, preferably in a lithographic printing process or a screen printing process in view of their increased photocure speeds and their increased depth hardness over the normally used thioxanthone derivatives.

The invention also concerns products applied with a photocured surface coating made by application of the photocurable composition as described hereinbefore.

The invention is illustrated by the following examples.

EXAMPLE 1

1-Chloro-4-Hydroxythioxanthone 2,2'-Dithiobisbenzoic acid (15.3 g; 0.05 mol) was stirred in concentrated sulphuric acid (150 ml) and 4-chlorophenol (38.5; 0.3) added over two hours at 10°–20° C. After stirring for a further hour the temperature was raised to 70°–80° for 2 hours. The mixture was cooled and quenched on to water (500 ml) and the resulting slurry cooled. The solid was filtered off, washed well with cold water and dried at 60° to give the title compound (18.3 g; 69.7%) of mp 260°–265° C.

EXAMPLE 2

1-Chloro-4-n-propoxythioxanthone

1-Chloro-4-hydroxythioxanthone (7.8 g; 0.03 mol) prepared as above and potassium carbonate (5.0 g; 0.036 mol) was stirred and refluxed for 10 minutes in acetone (50 ml). n-Propyl bromide (5.5 g; 0.045 mol) was added and the resulting mixture heated under reflux for 16 hours. The mixture was then cooled and quenched on to water (250 ml). The solid was filtered and washed with water the resulting damp solid recrystallised from ethanol (50 ml) to afford the title compound (6.9 g; 75.5%) of mp 102°–3°. Analysis $C_{16}H_{13}ClO_2S = 304.777$ Requires C 63.05%; H 4.30%; Cl 11.63%; S 10.52% Found C 63.14%; H 4.37%; Cl 11.66%; S 10.63%

EXAMPLE 3

1,3-Dichloro-4-n-propoxythioxanthone

Similarly prepared as in Examples 1 and 2, the title compound was prepared of mp 104°–105°. Analysis $C_{16}H_{12}Cl_2O_2S = 339.24$ Requires C 56.64% H 3.57% Cl 20.90% S 9.45% Found C 56.52 H 3.61% Cl 20.88% S 9.47%

EXAMPLE 4

4-Benzyloxy-1-chlorothioxanthone

Similarly prepared as in Examples 1 and 2, the title compound was prepared of mp 139°–40°. Analysis $C_{20}H_{13}ClO_2S$ Requires C 68.08% H 3.71% Cl 10.05% S 9.09% Found C 68.34 H 3.85% Cl 10.13% S 9.17%

EXAMPLE 5

4-Isoamyloxy-1-chlorothioxanthone

Similarly prepared as in Examples 1 and 2, the title compound was prepared of mp 96°–97°. Analysis $C_{18}H_{17}ClO_2S = 332.84$ Requires C 64.95% H 5.14% Cl 10.65% S 9.63% Found C 64.80% H 5.15% Cl 10.67% S 9.81%

EXAMPLE 6

1-Chloro-3-methyl-4-n-propoxythioxanthone

Similarly prepared in Examples 1 and 2, the title compound was prepared of mp 101°–103°. Analysis $C_{17}H_{15}ClO_2S = 318.81$ Requires C 64.04% H 4.74% Cl 11.12% S 10.06% Found C 63.78% H 4.79% Cl 11.19% S 10.06%

EXAMPLE 7

1-Fluoro-4-n-propoxythioxanthone

Similarly prepared as in Examples 1 and 2, the title compound was prepared of mp 125°–127°. Analysis $C_{16}H_{13}FO_2S$ Requires C 66.65% H 4.54% F 6.59% S 11.12% Found C 66.53% H 4.66% Cl 6.53% S 11.07%

EXAMPLE 8

4-Allyloxy-1-chlorothioxanthone

Similarly prepared as in Examples 1 and 2, the title compound was prepared of mp 135°–136°. Analysis $C_{16}H_{11}ClO_2S = 302.77$ Requires C 63.47% H 3.66% Found C 63.7% H 3.71%

EXAMPLE 9

3-Chloro-2-n-propoxythioxanthone

Similarly prepared as in Examples 1 and 2, the title compound was prepared of mp 101°–102°. Analysis $C_{16}H_{13}ClO_2S = 304.78$ Requires C 63.57% H 4.30% Found C 63.22% H 4.35%

EXAMPLE 10

1-Chloro-4-octyloxythioxanthone

Similarly prepared as in Examples 1 and 2, the title compound was prepared of mp 86°–87.5°. Analysis $C_{21}H_{23}ClO_2S = 374.92$ Requires C 67.27% H 6.18% Found C 67.08% H 6.14%

EXAMPLE 11

1-Chloro-2-methyl-4-n-propoxythioxanthone

Similarly prepared as in Examples 1 and 2, the title compound was prepared of mp 116.5°–117.5°. Analysis $C_{17}H_{15}ClO_2S = 318.81$ Requires C 64.04% H 4.74% Cl 11.12% Found C 64.23% H 4.79%

EXAMPLE 12

1-Bromo-4-n-propoxythioxanthone

Similarly prepared as in Examples 1 and 2, the title compound was prepared of mp 112.5°–113.5°. Analysis $C_{16}H_{13}BrO_2S = 349.25$ Requires C 55.02% H 3.75% Br 22.88% S 9.18% Found C 55.29% H 3.77%

EXAMPLE 13

1,4-Dimethoxythioxanthone

Similarly prepared as in Examples 1 and 2, the title compound was prepared of mp 201°–202°. Analysis $C_{15}H_{12}ClO_3S = 272.31$ Requires C 66.16% H 4.44% S 11.78% Found C 66.18% H 4.53% S 11.78%

EXAMPLE 14

1-Chloro-4-isopropoxythioxanthone

Similarly prepared as in Examples 1 and 2, the title compound was prepared of mp 91°–93°. Analysis $C_{16}H_{13}ClO_2S=304.78$ Requires C 63.05% H 4.30% Cl 11.63% S 10.52% Found C 63.15% H 4.32%

EXAMPLE 15

4-(Benzoylmethoxy)-1-chlorothioxanthone

Similarly prepared as in Examples 1 and 2, the title compound was prepared of mp 174°–176°. Analysis $C_{21}H_{13}ClO_3S=380.84$ Requires C 66.22% H 3.44% Cl 9.31% S 8.42% Found C 66.39% H 3.54% Cl 9.29% S 8.27%

EXAMPLE 16

2-(1-Chloro-4-thioxanthenyloxy)ethylpropenoate

Similarly prepared as in Examples 1 and 2, the title compound was prepared of mp 90°–91°. Analysis $C_{18}H_{13}ClO_4S=360.81$ Requires C 59.92% H 3.63% Cl 19.83% Found C 59.91% H 3.70%

EXAMPLE 17

4-Acetyloxy-1-chlorothioxanthone

1-Chloro-4-hydroxythioxanthone as prepared in Example 1 (13.1 g) and pyridine (10 g) was stirred in acetone (50 ml) at 50°. Acetyl chloride (4.3 g) was added over 0.25 h and the mixture stirred and heated under reflux for a further hour. The mixture was cooled to 20° and quenched with water (150 ml). The resulting solution was extracted with chloroform (50 ml), separated and the organic phase washed twice with water. The organic phase was evaporated to dryness under reduced pressure and the residue crystallised from methanol with a carbon treatment to afford the title compound, 4.1 g (27.0%) as a pale yellow solid of mp 141°–42°. Analysis $C_{15}H_9ClO_3S=304.745$ Requires C 59.11% H 2.98% Cl 11.63% S 10.52% Found C 59.10% H 3.06% Cl 11.59% S 10.41%

EXAMPLE 18

4-Benzoyloxy-1-chlorothioxanthone

1-Chloro-4-hydroxythioxanthone as prepared in Example 1 (6.6 g), potassium carbonate (4.1 g), 2-butanone (60 ml) and water (6 ml) were heated under reflux. Benzoyl chloride (5.3 g) was added over 20 minutes and the mixture heated under reflux for 3 hours. A solid precipitated from solution during the heating period. The mixture was cooled, quenched with water (120 ml), the solid filtered and recrystallised from 2-butanone with a charcoal treatment. The title compound (6.8 g; 74.0%) was obtained of mp 177°–78°. Analysis $C_{20}H_{11}ClO_3S=366.81$ Requires C 65.48% H 3.02% Cl 9.67% S 8.74% Found C 65.46% H 3.13% Cl 9.77% S 8.70%

EXAMPLE 19

1-Chloro-4-thioxanthenyl propenoate

Similarly prepared as in Example 18, the title compound was obtained in 48.1% yield as a pale yellow solid of mp 164°–165°. Analysis $C_{16}H_9ClO_3S=316.76$ Requires C 60.67% H 2.86% Cl 11.19% S 10.12% Found C 60.57% H 2.94% Cl 11.42% S 10.01%

EXAMPLE 20

Comparison of the efficiency of the compounds synthesised with Isopropylthioxanthone A method of assessing photoinitiator efficiency involves measuring the cure speed of a coating by counting the number of passes through a Primarc Minicure Unit to give a coating hardness measured by 2H pencil scratch. The minimum number of passes required to produce a scratch free surface is a measure of the cure speed; the lower the number of passes the higher the cure speed.

A blue urethane based screen ink was loaded with 2 molar % photoinitiator and 3% methyldiethanolamine and a 12μ coating of ink made on glass slides by a No. 2 Bar Coatere. A uv Minicure Unit composed of a single 80 Watts $cm^{-1}$ lamp was run with a belt speed of 60 rpm and the coated glass slide passed through the machine a number of times until a 2H pencil no longer marked the surface. The number of passes was recorded as a measure of cure speed.

| Example Number | Long Wave Abs (nm) | E(1 cm; 1%) | Number of Passes 2H |
|---|---|---|---|
| 2-isopropylthoxanthone (for comparison) | 383 | 207 | 13 |
| 2 | 387 | 175 | 6 |
| 3 | 383 | 161 | 7 |
| 4 | 390 | 167 | 5 |
| 5 | 390 | 173 | 6 |
| 6 | 383 | 175 | 6 |
| 7 | 387 | 153 | 6 |
| 8 | 390 | 186 | 6 |
| 9 | 390 | 192 | 7 |
| 10 | 392 | 161 | 6 |
| 11 | 395 | 175 | 5 |
| 12 | 391 | 172 | 14 |
| 13 | 398 | 232 | 11 |
| 14 | 392 | 177 | 5 |
| 15 | 390 | 170 | 10 |
| 16 | 390 | 153 | 6 |

EXAMPLE 21

Comparison of the efficiency of the compound of Example 2 with a known photoinitiator A blue litho ink was loaded with 3% benzophenone, 3% of ethyl p-dimethylaminobenzoate as amine synergist and 3% photoinitiator. The ink was coated at 1.5 thickness on to white card using a PIP Proofer and then passed through a Minicure UV unit running at 60 rpm for the minimum number of passes to give a hard tack free surface as defined by the Thumb Twist test. The number of passes was then related to the belt speed to give a cure speed. Comparison was made with isopropylthioxanthone which is widely used in litho inks.

| | Cure Speed |
|---|---|
| 2-Isopropylthioxanthone | 18.6 $ms^{-1}$ |
| 1-Chloro-4-propoxythioxanthone | 23.2 $ms^{-1}$ |

In screen inks the hardness of the coating is measured to give some measure to the depth of cure achieved for thick coatings. Hardness is measured by a Koenig Pendulum Hardness machine where a steel ball attacked to a pendulum is placed on the surface coating. The oscillation of the pendulum is measured to follow the damping effect of the surface coating on the rocking steel ball. A hard surface will have little damping effect compared with a soft surface and will lead to higher oscillation figures. An epoxy acrylate resin was loaded with 2% benzophenone, 3% methyldiethanolamine as co-initiator and 2% initiator. This was coated at 50 thickness on to glass slides and cured in the Minicure unit at 2.5 ms$^{-1}$. The coatings were allowed to stand for 24 hours and the Pendulum Hardness measured. An average of 5 readings taken on different parts of the surface was noted. Comparison was made with 2-isopropyl-thioxanthone as photoinitiator.

|  | Pendulum Hardness |
| --- | --- |
| 2-Isopropylthioxanthone | 93 s |
| 1-Chloro-4-propoxythioxanthone | 115 s |

The above figures represent a clear advance over known photoinitiators and illustrate the invention.

We claim:

1. Thioxanthone derivatives of the formula:

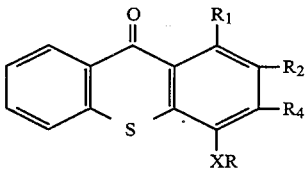

wherein
$R_1$ is Cl or Br;
$R_2$ is hydrogen or $C_{1-6}$ alkyl;
X is an oxygen or sulfur atom;
$R_4$ is hydrogen, Cl, Br or a $C_{1-6}$ alkyl group; and
$R_3$ is a $C_{2-10}$ alkyl group, optionally substituted by a hydroxy group which hydroxy group may be alkylated by an optionally substituted $C_{1-6}$ alkyl, $C_{2-6}$ alkenyl or a benzyl group or acylated by a $C_{1-8}$ alkanoyl or a $C_{2-8}$ alkenoyl group; a $C_{2-10}$ alkenyl group, a $C_{3-6}$ cycloalkyl group, a $C_{1-8}$ alkanoyl group, a $C_{2-8}$ alkenoyl group, an optionally substituted phenyl group, or an optionally substituted benzoyl group.

2. A compound according to claim 1 wherein $R_1$ is Cl.

3. A compound according to claim 1 wherein X is oxygen.

4. A compound according to claim 3 wherein $R_1$ is Cl or Br and $R_3$ is a $C_{2-10}$ alkyl group.

5. A compound according to claim 3 wherein $R_1$ is Br and $R_2$ and $R_4$ are hydrogen.

6. A compound according to claim 3 wherein $R_1$ is Cl.

7. A compound according to claim 4 wherein $R_2$ and $R_4$ are hydrogen.

8. A compound according to claim 6 wherein $R_3$ is optionally substituted $C_{2-10}$ alkyl.

9. A compound according to claim 6 wherein $R_3$ is $C_{2-10}$ alkenyl.

10. A compound according to claim 6 wherein $R_3$ is $C_{3-6}$ cycloalkyl.

11. A compound according to claim 6 wherein $R_3$ is a $C_{1-8}$ alkanoyl group.

12. A compound according to claim 6 wherein $R_3$ is a $C_{2-8}$ alkenoyl group.

13. A compound according to claim 6 wherein $R_3$ is an optionally substituted phenyl group.

14. A compound according to claim 6 wherein $R_3$ is an optionally substituted benzoyl group.

15. A compound according to claim 6 wherein $R_2$ is hydrogen, $R_4$ is Cl and $R_3$ is n-propyl.

16. A compound according to claim 6 wherein $R_2$ and $R_4$ are hydrogen and $R_3$ is allyl.

17. A compound according to claim 6 wherein $R_2$ and $R_4$ are hydrogen and $R_3$ is isoamyl.

18. A compound according to claim 6 wherein $R_2$ is hydrogen, $R_4$ is methyl and $R_3$ is n-propyl.

19. A compound according to claim 6 wherein $R_2$ and $R_4$ are hydrogen and $R_3$ is octyl.

20. A compound according to claim 6 wherein $R_2$ is methyl, $R_4$ is hydrogen and $R_3$ is n-propyl.

21. A compound according to claim 6 wherein $R_2$ and $R_4$ are hydrogen and $R_3$ is isopropyl.

22. 1-chloro-4-n-propoxy thioxanthone.

23. 3-chloro-2-alkoxy thioxanthone where the alkoxy group has from 2–10 carbon atoms.

24. A compound of claim 23 wherein the alkoxy is n-propoxy.

25. 1-bromo-4-n-propoxy thioxanthone.

* * * * *

UNITED STATES PATENT AND TRADEMARK OFFICE
CERTIFICATE OF CORRECTION

PATENT NO. : 5,414,092

DATED : May 9, 1995

INVENTOR(S) : WILLIAM A. GREEN ET AL.

It is certified that error appears in the above-identified patent and that said Letters Patent is hereby corrected as shown below:

In claim 1, column 7, the formula should read as follows:

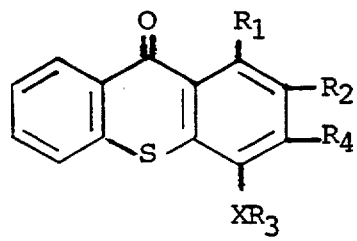

Signed and Sealed this

Fifteenth Day of August, 1995

Attest:

BRUCE LEHMAN

Attesting Officer   Commissioner of Patents and Trademarks